(12) United States Patent
Kelly

(10) Patent No.: US 6,530,892 B1
(45) Date of Patent: Mar. 11, 2003

(54) AUTOMATIC SKIN PUNCTURING SYSTEM

(76) Inventor: Helen V. Kelly, 1650 Sunset Strip, Sunrise, FL (US) 33313

( * ) Notice: Subject to any disclaimer, the term of this patent is extended or adjusted under 35 U.S.C. 154(b) by 0 days.

(21) Appl. No.: 09/801,331

(22) Filed: Mar. 7, 2001

(51) Int. Cl.[7] .............................. A61B 5/15; A61B 10/00
(52) U.S. Cl. ...................................................... 600/583
(58) Field of Search ......................................... 600/583

(56) References Cited

U.S. PATENT DOCUMENTS

| | | | |
|---|---|---|---|
| 3,626,929 A | * 12/1971 | Sanz et al. ................... | 600/583 |
| 4,924,879 A | * 5/1990 | O'Brien ....................... | 600/583 |
| 5,054,499 A | * 10/1991 | Swierczek ................... | 600/583 |
| 5,487,748 A | * 1/1996 | Marshall et al. ............ | 600/583 |
| 5,682,233 A | * 10/1997 | Brinda ........................ | 600/583 |
| 5,730,753 A | * 3/1998 | Morita ........................ | 600/583 |
| 5,971,941 A | * 10/1999 | Simons et al. .............. | 600/583 |
| 6,155,992 A | * 12/2000 | Henning et al. ............ | 600/583 |

* cited by examiner

*Primary Examiner*—Paul J. Hirsch

(57) ABSTRACT

An automatic skin puncturing system that was operable with one hand for allowing individuals with the use of only a single hand to take the blood samples needed to monitor their blood glucose levels. The automatic skin puncturing system includes a housing assembly, a power connecting jack, a battery holder, an indexable, motor driven turntable, an index switch, a reed switch, a lancet lifting assembly, a disposable lancet carousel cartridge, and an electronic, micro-processor controlled circuit.

1 Claim, 13 Drawing Sheets

AUTOMATIC SKIN PUNCTURING SYSTEM

TECHNICAL FIELD

The present invention relates to medical accessories and more particularly to an automatic skin puncturing system that is operable with one hand to allow an individual paralyzed on one side to take a blood sample from a finger tip for use in blood glucose level monitoring.

BACKGROUND ART

Many individuals suffer strokes and other paralyzing afflictions that render them paralyzed on one side of their bodies. Such paralysis limits the activities that can be performed by these individuals. In most cases, individuals with the use of only one half of their bodies cannot perform the physicals steps necessary to use a lancet to take a blood sample from their finger tip. Such a limitation can be life threatening for individuals who must monitor their blood glucose level on a regular basis in order to prevent diabetic comas, and other serious consequence of out of limit blood glucose levels. It wold be desirable, therefore, to have an automatic skin puncturing system that was operable with one hand for allowing individuals with the use of only a single hand to take the blood samples needed to monitor their blood glucose levels.

GENERAL SUMMARY DISCUSSION OF INVENTION

It is thus an object of the invention to provide an automatic skin puncturing system that is operable with one hand to allow an individual paralyzed on one side to take a blood sample from a finger tip for use in blood glucose level monitoring.

Accordingly, an automatic skin puncturing system is provided. The an automatic skin puncturing system includes a housing assembly, a power connecting jack, a battery holder, an indexable, motor driven turntable, an index switch, a reed switch, a lancet lifting assembly, a disposable lancet carousel cartridge, and an electronic, micro-processor controlled circuit; the housing assembly including a bottom housing portion, a removable housing carousel cover portion and a securing knob; the bottom housing portion having a puncturing system cavity defined therein and accessible through a cartridge positioning opening formed through a top bottom housing portion surface, a triggering magnet opening formed through the top bottom housing portion surface at a location adjacent to the cartridge positioning opening, a power connecting jack opening, a battery compartment access cover, a counter display, an on/off switch, and a number of nonskid foot pads; the removable housing carousel cover portion being sized and securable to the bottom housing portion in a manner to cover the cartridge positioning opening with the securing knob, the removable housing carousel cover portion including a pivoting lancet lifting assembly trigger switch actuator having a top switch surface portion that is hingedly connected to and pivots with respect to a top cover surface of the removable housing carousel cover portion and a reed switch triggering magnet connected to a rod mechanically carried by the top switch surface portion that is positioned through the triggering magnet opening of the bottom housing portion when the top switch surface portion is oriented in parallel with the top cover surface of the removable housing carousel cover portion, the top switch surface portion including a finger positioning indentation having a lancet passage opening formed therethrough; the power connecting jack being positioned within the puncturing system cavity of the housing and adjacent the power connecting jack opening; the battery holder being positioned within the puncturing system cavity of the housing within a battery compartment and accessible by battery compartment access cover; the indexable, motor driven turntable being rotatable within the puncturing system cavity of the housing on a bearing pivot point extending upward from a bottom surface of the housing, the indexable, motor driven turntable being driven by a dc motor having a gear in connection with a perimeter rack gear formed around the underside of the turntable, a keyed carousel cartridge drive shaft extending upwardly from a center thereof, and a perimeter side edge having a number of index switch roller indentations formed thereon; the index switch being positioned within the puncturing system cavity of the housing and with respect to the indexable, motor driven turntable such that a roller of the index switch rolls along the perimeter side edge indexable, motor driven turntable; the index switch having open index switch contacts when the roller is positioned in one of the number of index switch roller indentations and closed open index switch contacts when the roller is not positioned in one of the number of index switch roller indentations; the reed switch being positioned within the housing at a location such that the reed switch triggering magnet is position in a location to close a pair of reed switch contacts when a user pushes down on the top switch surface portion; the lancet lifting assembly being positioned within the puncturing system cavity of the housing and including a main plate and a linear sliding, wedge shaped lift rod raising cam connected to the end of a lancet lifting assembly solenoid attached to the main plate; the lancet lifting assembly solenoid moving the wedge shaped lift rod raising cam along a linear path between a first cam position and a second cam position; the main plate having an adjustment wheel contact structure extending from a solenoid side end thereof; the main plate being supported by a main plate support fulcrum positioned under a cam side end of the main plate and contact between the adjustment wheel contact structure and an angled undersurface of a lancet depth adjustment wheel rotatably mounted to the bottom housing portion such that a portion of the lancet depth adjustment wheel extends out of the bottom housing portion, the height of the cam side end of the main plate being adjustable by positioning the lancet depth adjustment wheel; the disposable lancet carousel cartridge including a cartridge housing having a carousel hub formed through the center thereof having a key way adapted for receiving the upwardly projecting keyed carousel cartridge drive shaft of the indexable motor driven turntable, an outer perimeter upper cartridge surface having a number of spaced lancet cartridge openings, and a number of lancet assemblies each with a lancet positioned beneath one of the number of spaced lancet cartridge openings and a lancet lift rod having a first end connected to the lancet and a second lift rod end slidably positioned through and past a cartridge bottom surface a distance such that a force pushing upward on the second lift rod end causes a puncturing tip of the lancet to be raised through and past its respective spaced lancet cartridge opening; the cartridge bottom surface being positioned above the linear path of the linear sliding, wedge shaped lift rod raising cam a distance such that, when a second lift rod end is positioned above the second cam position, movement of the wedge shaped lift rod raising cam from the first cam position to the second cam position results in contact between the wedge shaped lift rod raising cam and the second lift rod end sufficient to cause the puncturing tip of the lancet attached to the second lift rod end to be raised through and past its respective spaced lancet cartridge opening; the electronic, micro-processor controlled control circuit being in power receiving connection with the power connecting jack and the battery holder, in controlling connection with the lancet lifting assembly solenoid, the turntable motor drive circuit, and the counter display, and in input receiving connection from the counter reset switch, the on/off switch, and the reed switch; the turntable motor drive circuit being in controlling connection with the turntable drive motor and in input receiving connection with the turntable indexing switch; the electronic, micro-processor controlled control circuit being programmed to a) move the indexable, motor driven turntable until the puncturing tip of a lancet in alignment with the lancet passage opening when turned on with the on/off switch; b) wait until a trigger signal is received from the reed switch; c) operate the lancet lifting assembly solenoid to move the lift rod raising cam from the first cam position to the second cam position and then back to the first cam position, in response to receiving the trigger signal; d) move the indexable, motor driven turntable such that no puncturing tip of a lancet is in alignment with the lancet passage opening; and e) decrement the lancet counter display.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
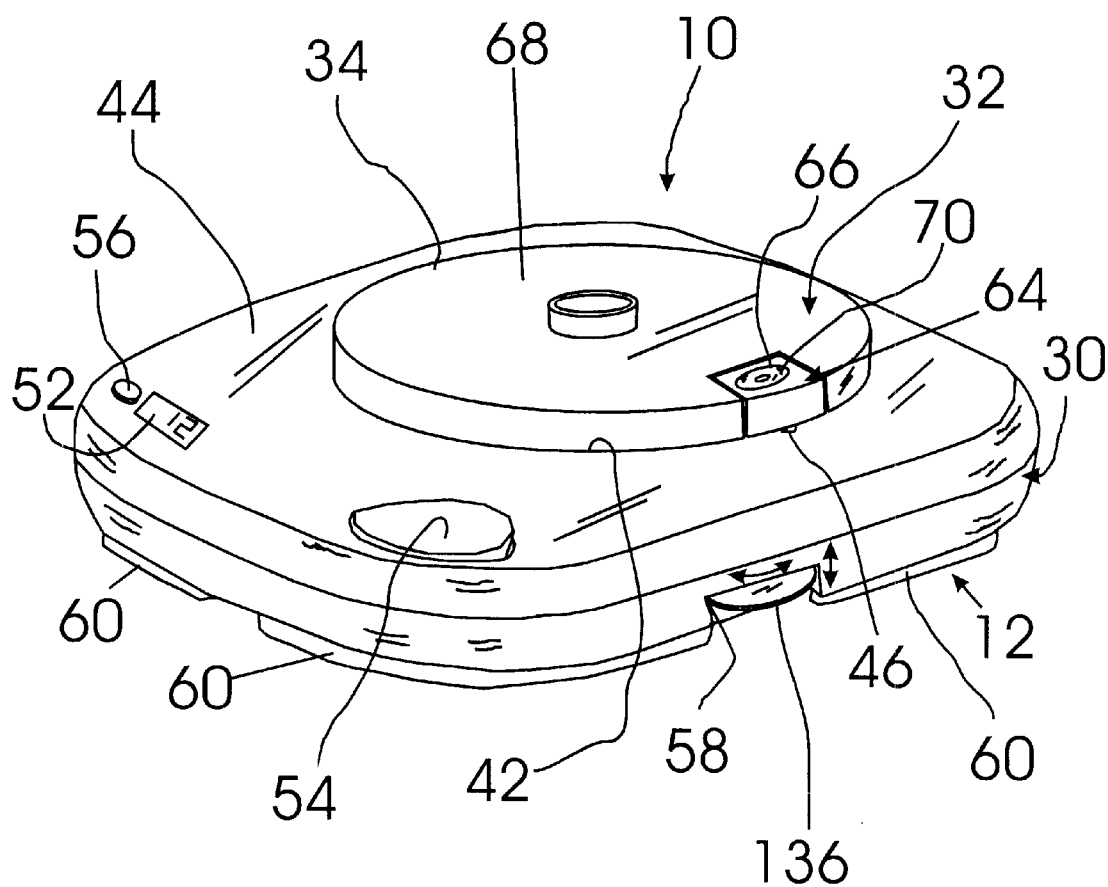
FIG. 1 is a perspective view of a first exemplary embodiment of the automatic skin puncturing system of the present invention.
Figure 2:
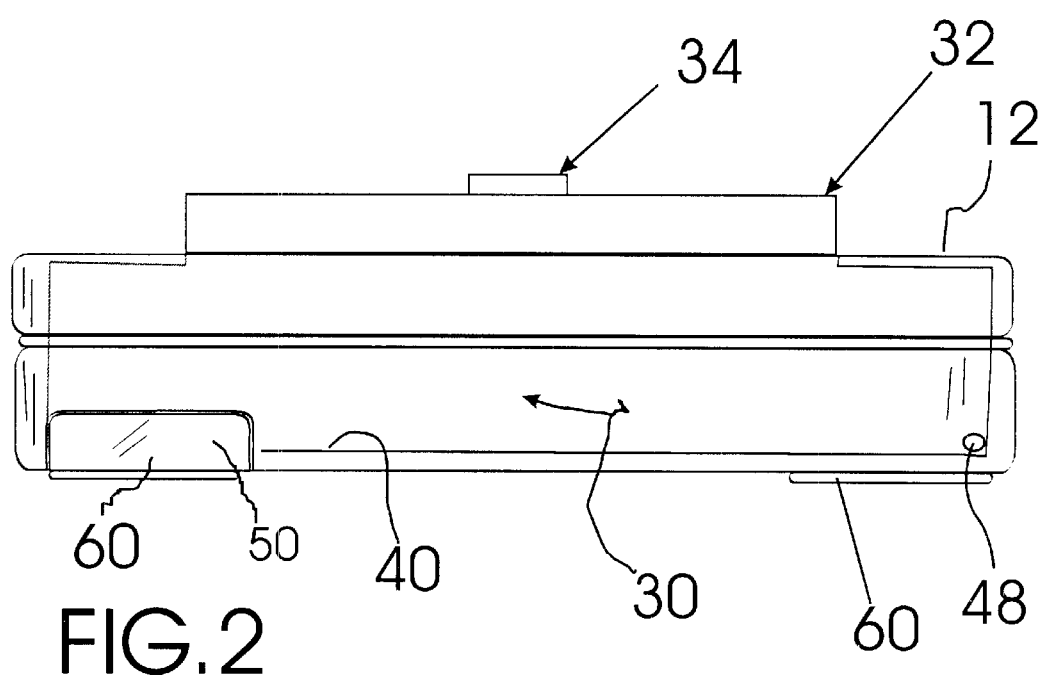
FIG. 2 is a back side plan view of the automatic skin puncturing system of FIG. 1 showing a power connecting jack and a battery compartment cover.
Figure 3:
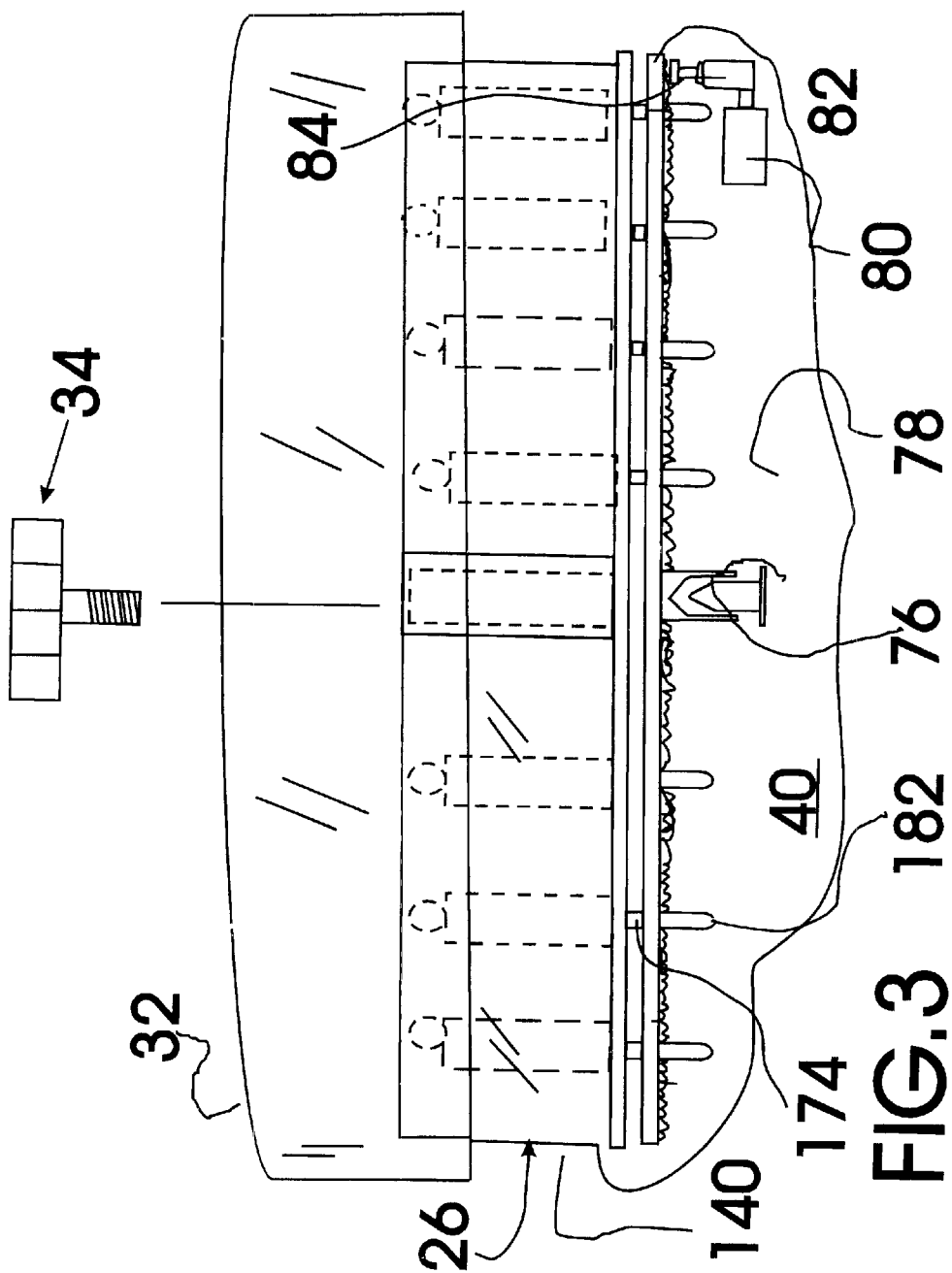
FIG. 3 is a partial side plan view of the housing carousel cover, the disposable lancet carousel cartridge, and the indexable, motor driven turntable rotatable on a bearing pivot point and driven by a dc motor having a gear in connection with a perimeter rack gear formed around the underside of the turntable.
Figure 4:
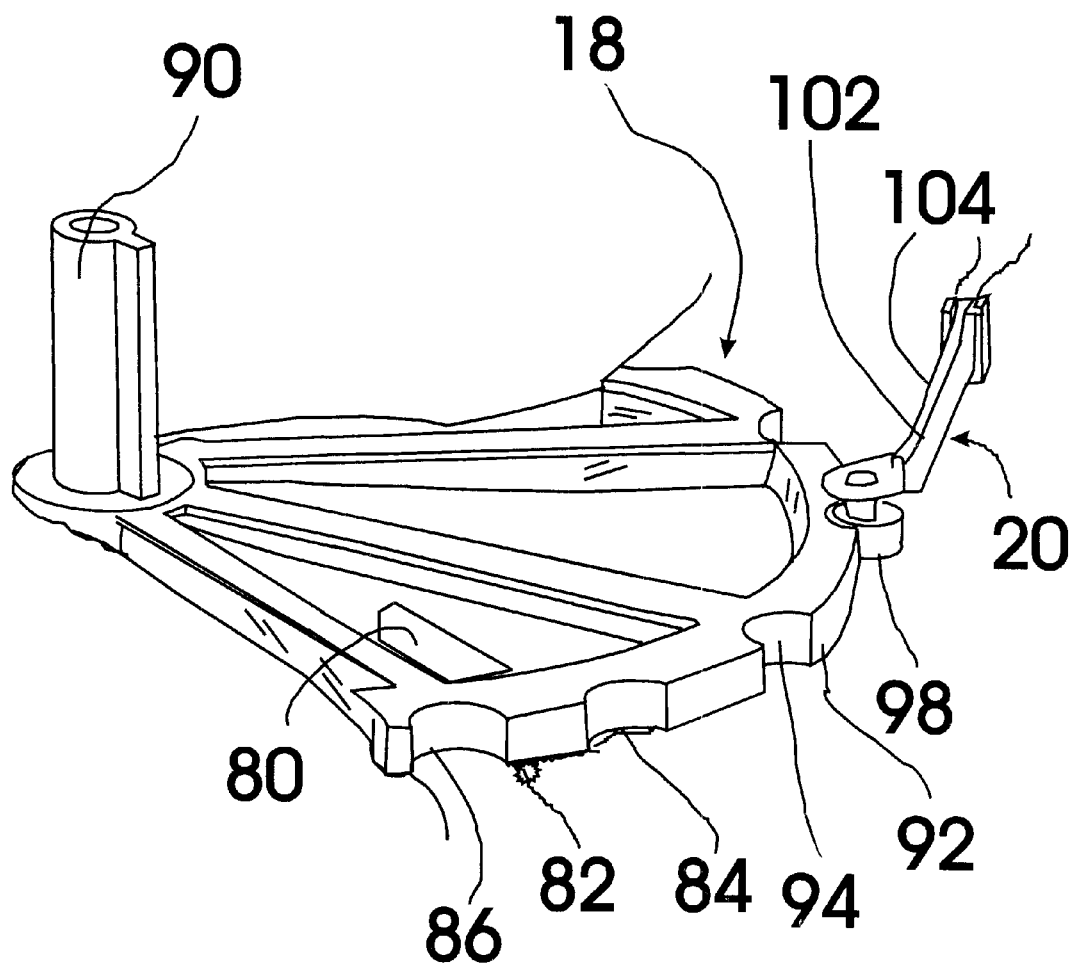
FIG. 4 is a perspective, detail view of a portion of the motor driven turntable showing the carousel cartridge drive hub, the indexing indentations on the perimeter side edge, and the dc motor control switch with the spring loaded wheel of the first switch contact riding on the side edge and the second switch contact positioned on a contact support plate adjacent the first switch contact.
Figure 5:
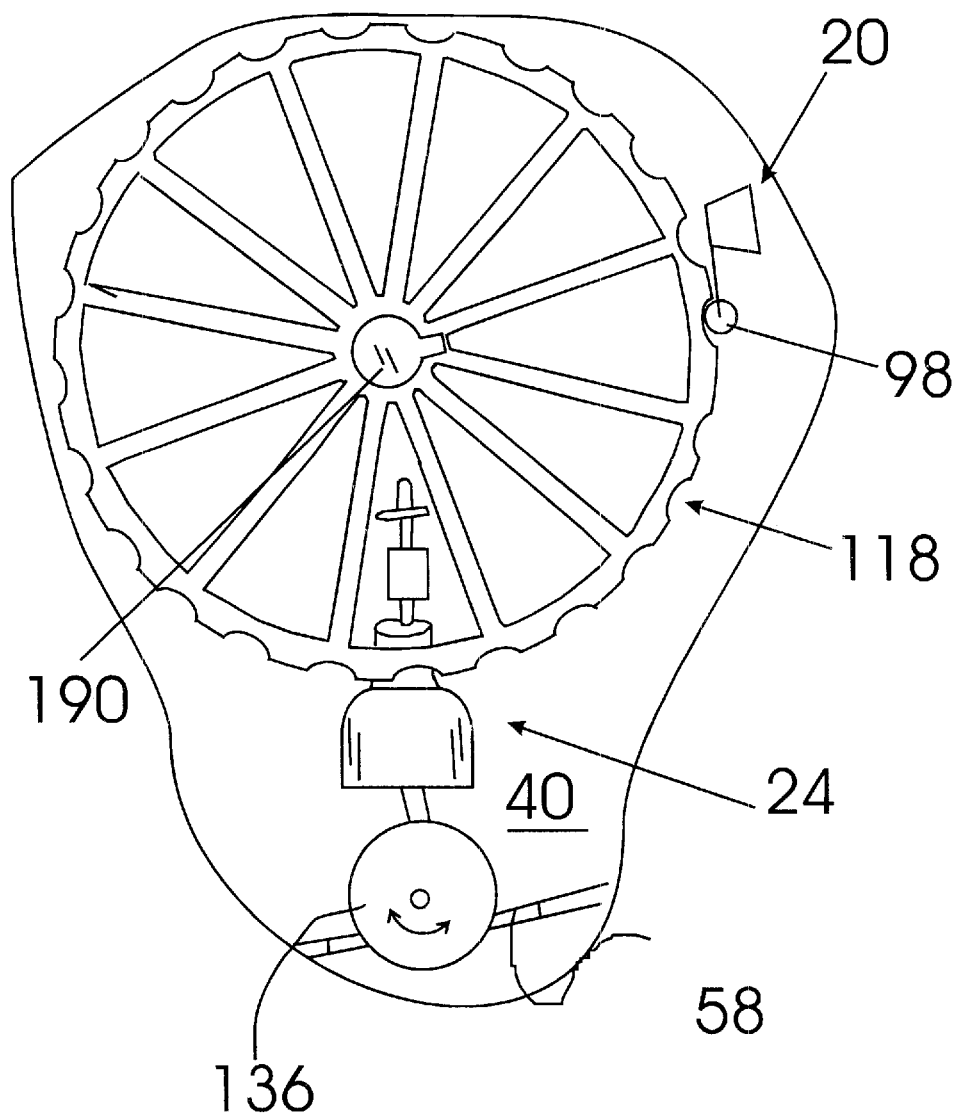
FIG. 5 is a top plan detail view showing the indexable, motor driven turntable including the upwardly projecting keyed carousel cartridge drive shaft, the lancet lifting assembly, and the lancet depth adjustment wheel.
Figure 6:
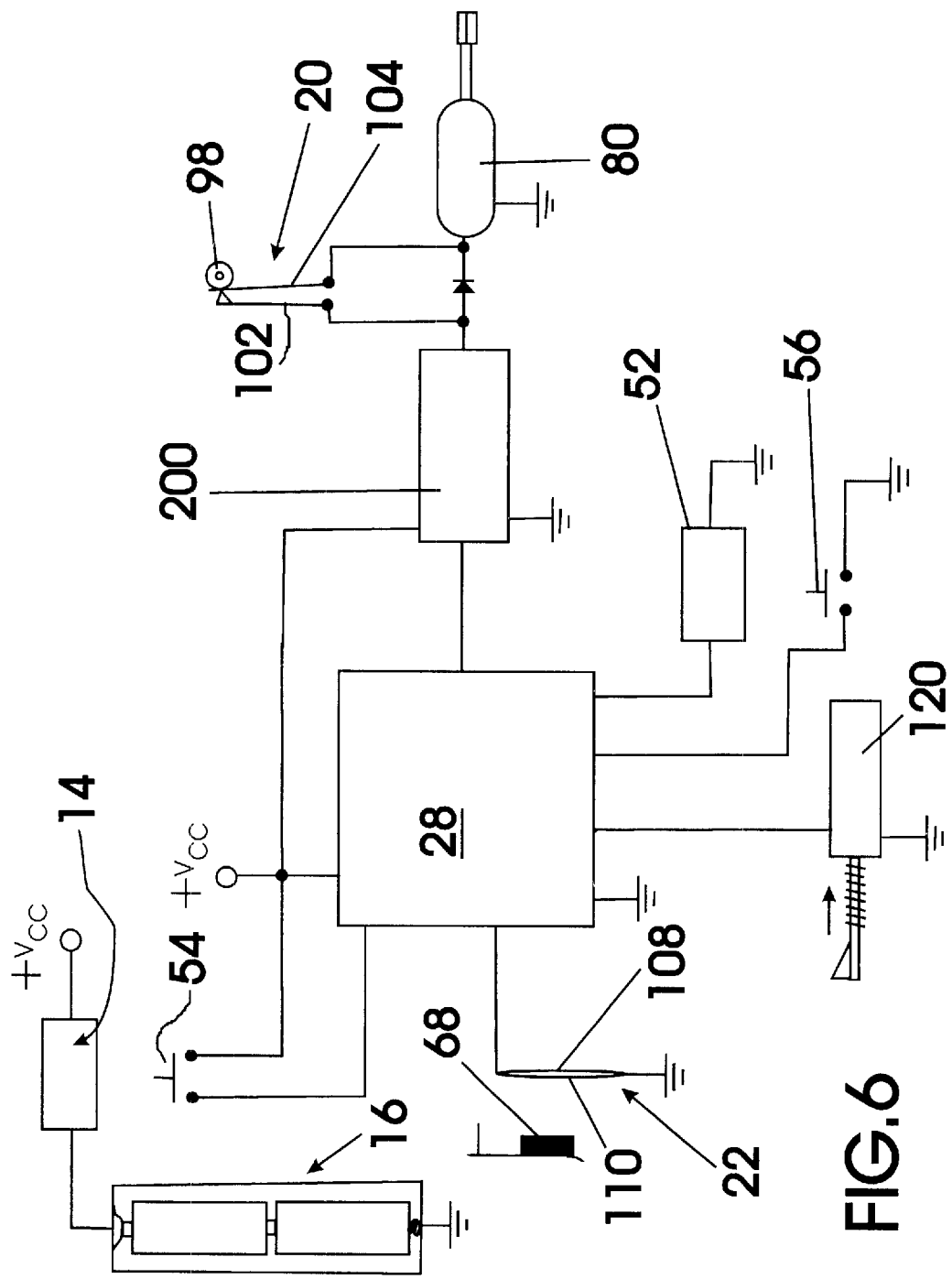
FIG. 6 is a schematic diagram of the electrical components of the automatic skin puncturing system of FIG. 1.
Figure 7:
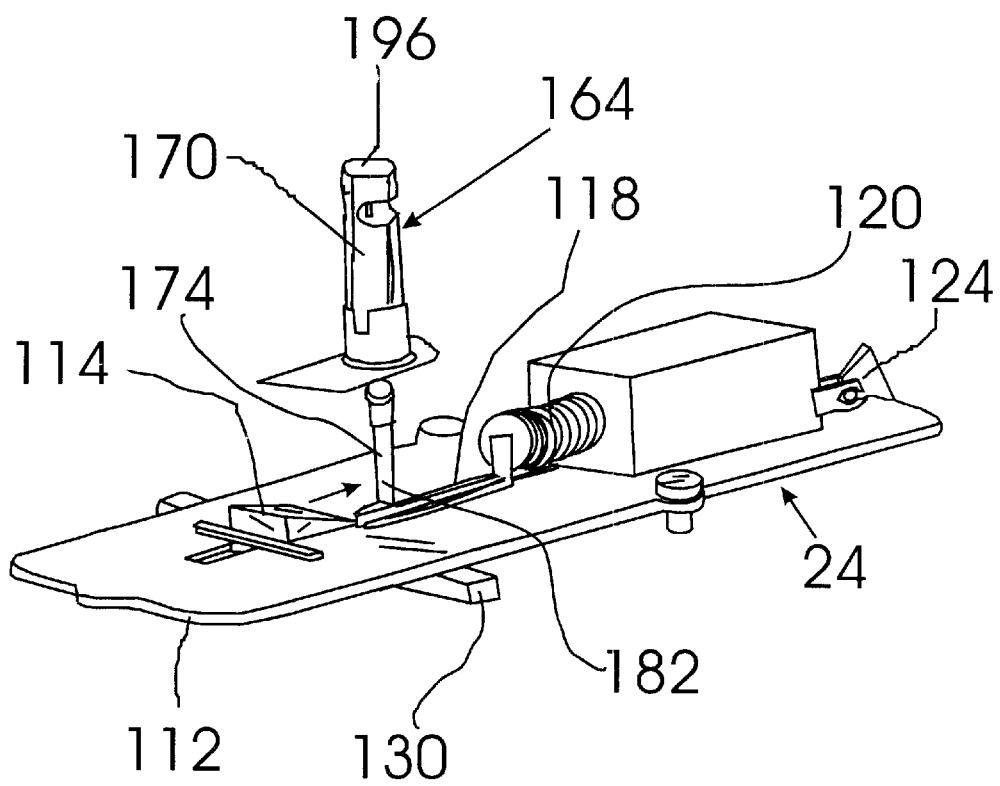
FIG. 7 is a perspective detail view of the lancet lifting assembly with the lancet lift rod of one of the lancet holding assemblies of the disposable lancet carousel cartridge in position ready to be forced upward when the linear cam is pulled toward the solenoid of the lancet lifting assembly.
Figure 8:
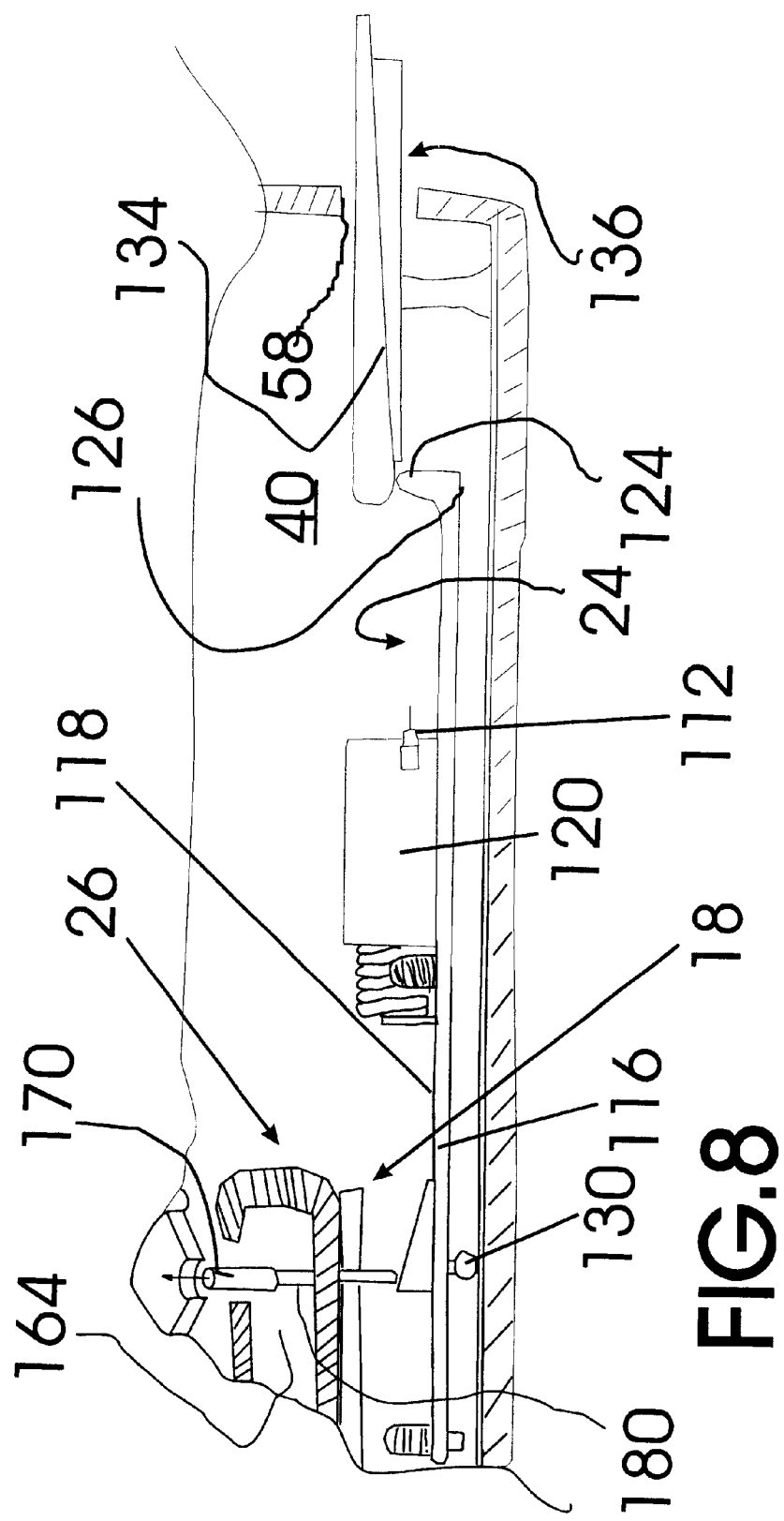
FIG. 8 is a side plan detail view the lancet lift rod of one of the lancet holding assemblies of the disposable lancet carousel cartridge in the lifted position after being forced upward as the solenoid pulls the linear cam toward itself; the angled undersurface of the lancet depth adjustment wheel in contact with the top of a lancet cam contact structure extending upward from a back end of the fulcrum supported main plate of lancet lifting assembly, and the lancet lifting assembly support springs extending downward from the main plate on either side of the main plate support fulcrum.
Figure 9:
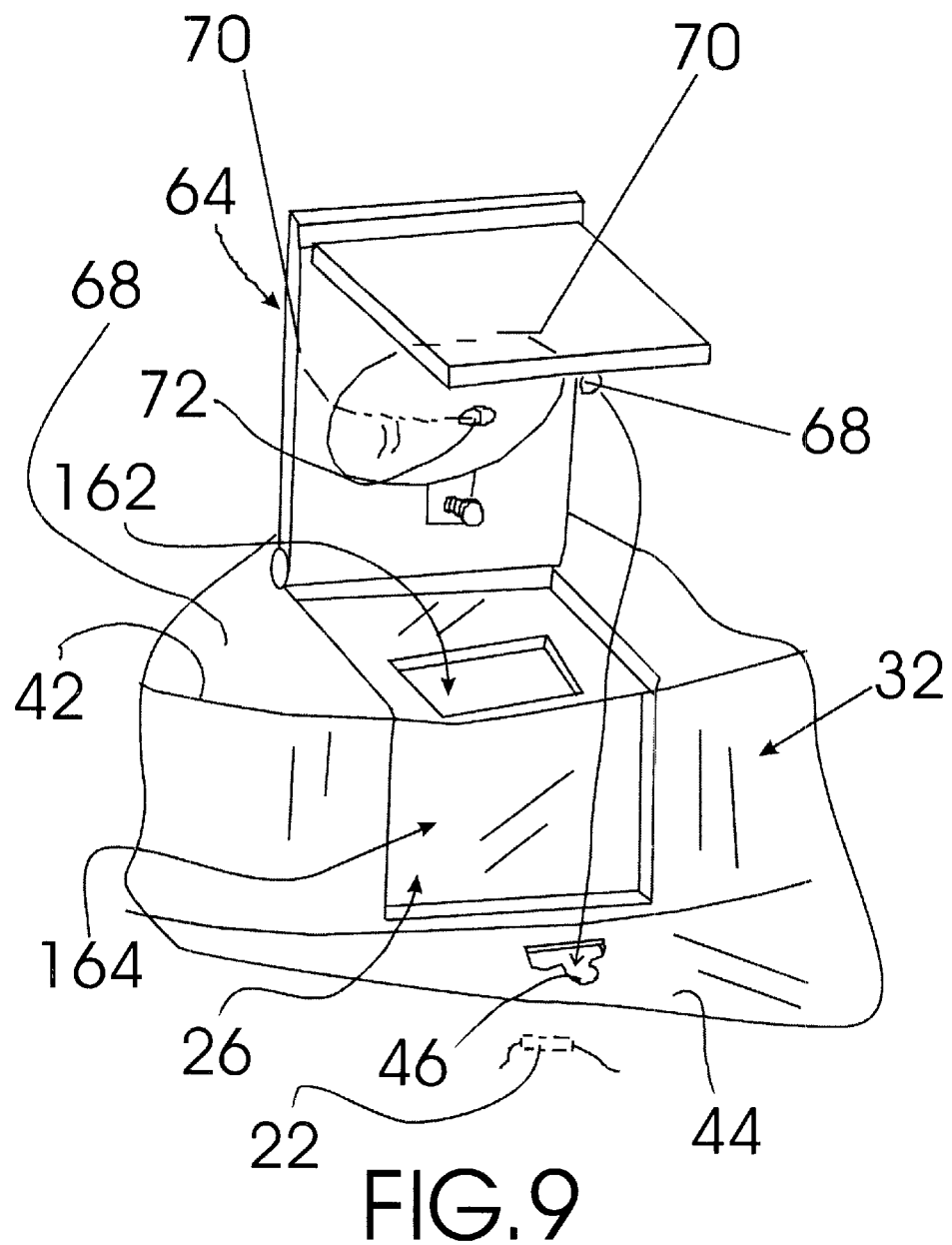
FIG. 9 is a partial detail perspective view showing a portion of the disposable lancet carousel cartridge showing the piercing point of a lancet; a lancet cartridge opening above the lancet; and the pivoting lancet lifting assembly trigger switch including the hinged portion of the removable carousel cover of the housing with the finger positioning indentation formed into the top of the hinged portion, the lancet passage opening through the hinged portion of the removable carousel cover of the housing at a location within the finger positioning indentation, a reed switch triggering magnet connected to a rod extending form a bottom edge of the hinged portion, a triggering magnet opening formed through a top surface of the housing and a reed switch positioned within the housing at a location such that the triggering magnet closes the reed switch when a user pushes down on the hinged portion.
Figure 10:
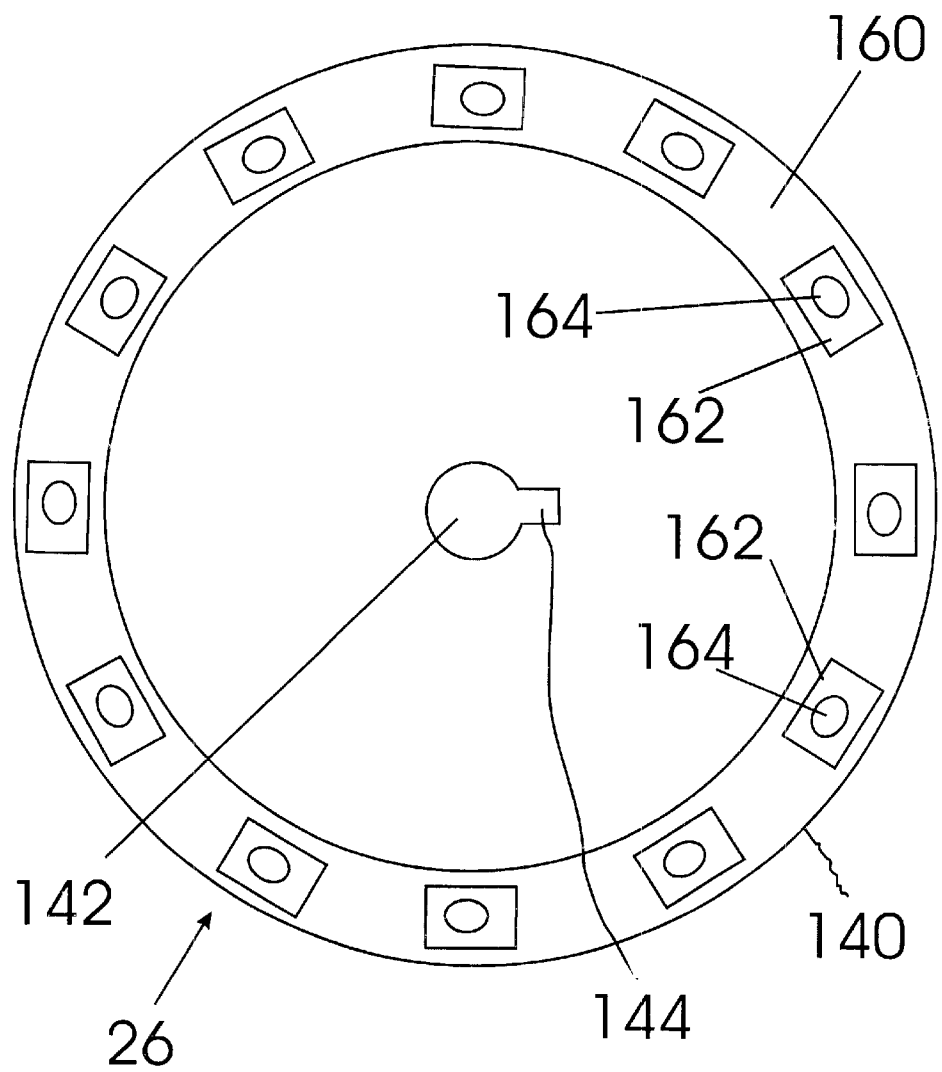
FIG. 10 is a top plan view of the disposable lancet carousel cartridge showing a lancet positioned within each of twelve spaced lancet cartridge openings and a carousel hub formed through the center of the disposable lancet carousel cartridge having a key way adapted for receiving the upwardly projecting keyed carousel cartridge drive shaft of the indexable, motor driven turntable.
Figure 11:
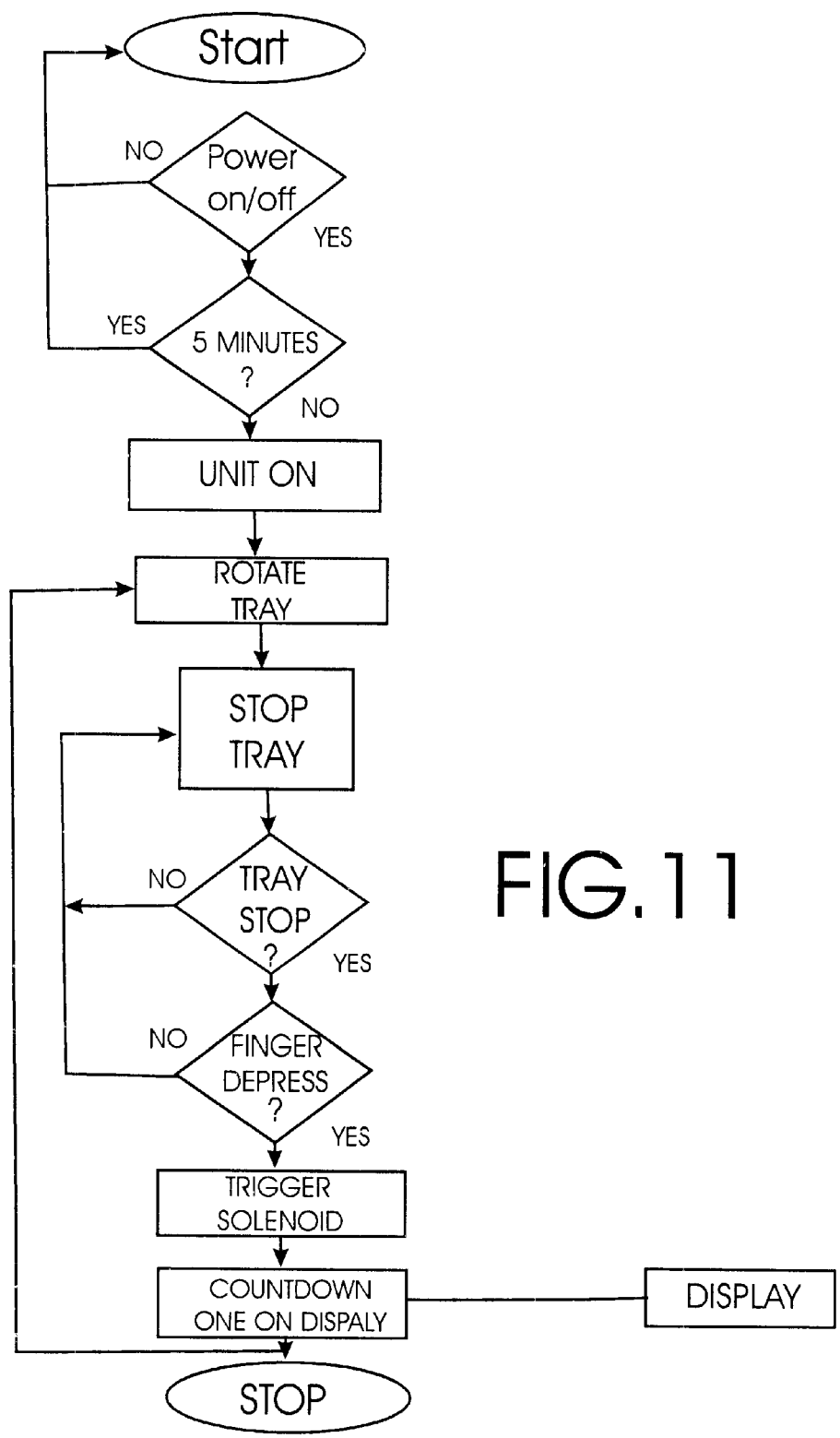
FIG. 11 is a flow chart of the micro-processor control program for the micro-processor of the automatic skin puncturing system.
Figure 12:
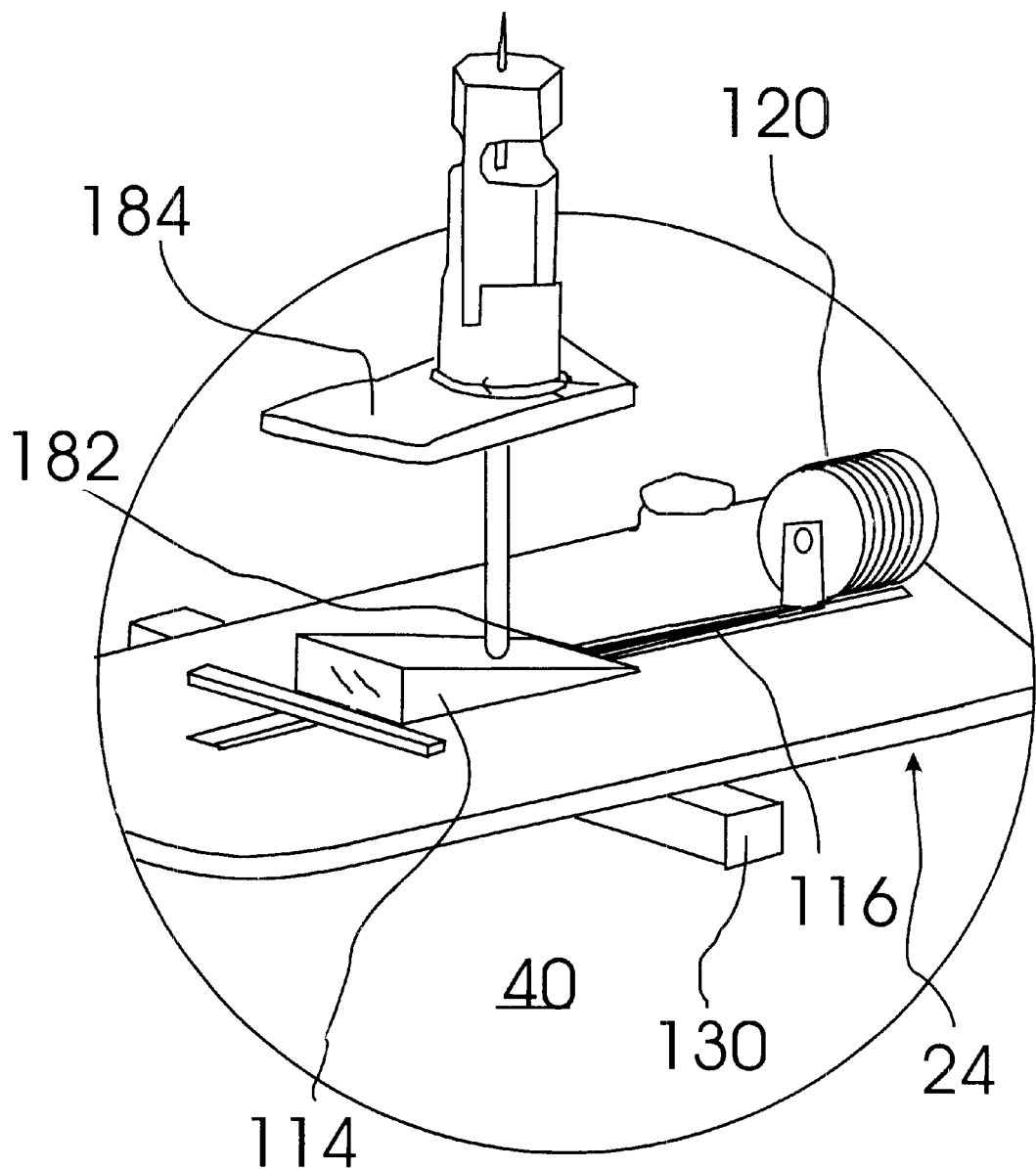
FIG. 12 is a detail perspective view showing the linear cam of the lancet lifting assembly in the extended position and the lancet lift rod of one of the lancet holding assemblies of the disposable lancet carousel cartridge in position ready to be forced upward when the linear cam is pulled toward the solenoid of the lancet lifting assembly.
Figure 13:
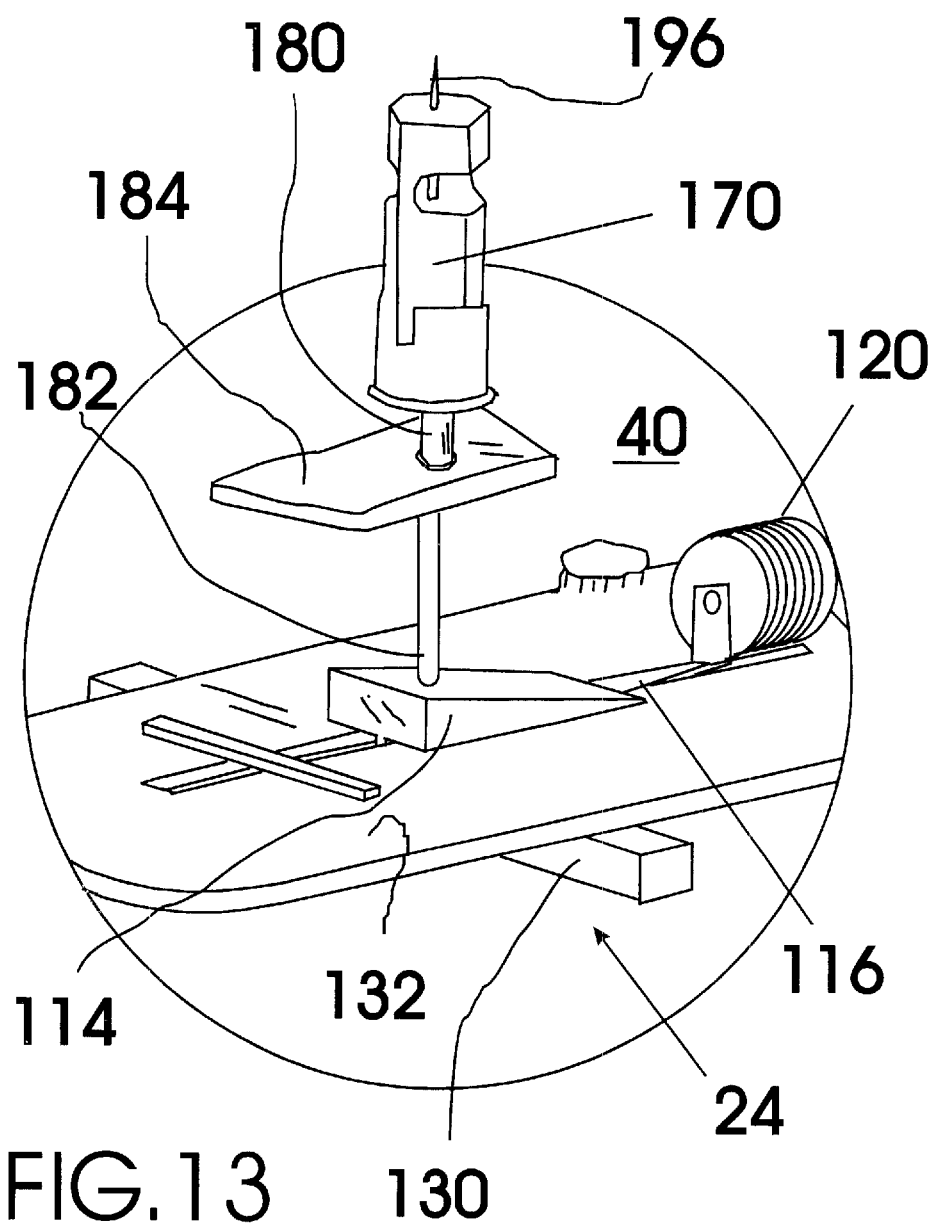
FIG. 13 is a detail perspective view showing the linear cam of the lancet lifting assembly in the retracted position and the lancet lift rod of one of the lancet holding assemblies of the disposable lancet carousel cartridge forced upward by the angled top surface of the linear cam.

FIGS. 1–13 show various aspects of an exemplary embodiment of the automatic skin puncturing system of the present invention generally designated 10. Automatic skin puncturing system 10 includes a housing assembly, generally designated 12; a power connecting jack, generally designated 14; a battery holder, generally designated 16; an indexable, motor driven turntable generally designated 18; an index switch, generally designated 20; a reed switch, generally designated 22; a lancet lifting assembly, generally designated 24; a disposable lancet carousel cartridge, generally designated 26; and an electronic, micro-processor controlled circuit, generally designated 28.

Housing assembly 12 includes a bottom housing portion, generally designated 30; a removable housing carousel cover portion, generally designated 32; and a securing knob 34

Bottom housing portion 30 has a puncturing system cavity, generally designated 40 (shown in dashed lines of FIG. 2) defined therein and accessible through a circular cartridge positioning opening 42 formed through a top bottom housing portion surface 44; a triggering magnet opening 46 formed through the top bottom housing portion surface 44 at a location adjacent to the cartridge positioning opening 42; a power connecting jack opening 48; a battery compartment access cover 50; a counter display 52; an on/off switch 54; a counter reset switch 56; an adjustment wheel opening 58 and a number of nonskid foot pads 60.

Removable housing carousel cover portion 32 is sized and securable to bottom housing portion 30 with securing knob 34 in a manner to cover the cartridge positioning opening 42. Removable housing carousel cover portion 32 includes a pivoting lancet lifting assembly trigger switch actuator, generally designated 64, having a top switch surface portion 66 that is hingedly connected to and pivots with respect to a top cover surface 68 of removable housing carousel cover portion 32 and a reed switch triggering magnet 68 connected to a rod 70 mechanically carried by top switch surface portion 66 that is positioned through triggering magnet opening 46 when top switch surface portion 66 is oriented in parallel with top cover surface 68 of removable housing carousel cover portion 32 as shown in FIG. 1. Top switch surface portion 66 includes a finger positioning indentation 70 having a lancet passage opening 72 formed therethrough.

Power connecting jack 14 and battery holder 16 are both positioned within puncturing system cavity 40.

Indexable, motor driven turntable 18 is rotatable within puncturing system cavity 40 on a bearing pivot point 76 extending upward from a bottom surface 78 of bottom housing portion 30. Indexable, motor driven turntable 18 is driven by a dc motor 80 having a gear 82 in connection with a perimeter rack gear 84 formed around the entire underside 86 of motor driven turntable 18. Motor driven turntable 18 also includes a keyed carousel cartridge drive shaft 90 extending upwardly from a center thereof, and a perimeter side edge surface 92 having a number of index switch roller indentations 94 spaced around the entre circumference thereof. Index switch 20 is positioned within puncturing system cavity 40 and with respect to indexable, motor driven turntable 18 such that a roller 98 of index switch 20 rolls along perimeter side edge surface 92 of indexable, motor driven turntable 18. Index switch 20 has open index switch contacts 102,104 when roller 98 is positioned in one of the number of index switch roller indentations 94 and closed open index switch contacts 102,104 when the roller is not positioned in one of the number of index switch roller indentations 94.

Reed switch 22 is positioned within housing 12 at a location such that reed switch triggering magnet 66 is position in a location to close a pair of reed switch contacts 108,110 when a user pushes forcefully down on top switch surface portion 66.

Lancet lifting assembly 24 is positioned within puncturing system cavity 40 and includes a main plate 112 and a linear sliding, wedge shaped lift rod raising cam 114 connected to the end 116 of an actuator shaft 118 of a lancet lifting assembly solenoid 120 attached to main plate 112. Lancet lifting assembly solenoid 120 moves wedge shaped lift rod raising cam 114 along a linear path between a first cam position (shown in FIGS. 7 and 12) and a second cam position (shown in FIGS. 8, and 13). Main plate 112 has an adjustment wheel contact structure 124 extending from a solenoid side end 126 thereof. Main plate 112 is adjustably supported by a main plate support fulcrum 130 positioned under a cam side end 132 of main plate 112 and contact between adjustment wheel contact structure 124 and an angled undersurface 134 of a lancet depth adjustment wheel 136 rotatably mounted to bottom housing portion 30. It can be seen that the height of the cam side end 132 of main plate 112 is adjustable by rotatably positioning the lancet depth adjustment wheel 136.

Disposable lancet carousel cartridge 26 includes a cartridge housing 140 having a carousel hub 142 formed through the center thereof having a key way 144 adapted for receiving the upwardly projecting keyed carousel cartridge drive shaft 90 of motor driven turntable 18, an outer perimeter upper cartridge surface 160 having a number of spaced lancet cartridge openings 162, and a number of lancet assemblies, generally designated 164, each with a lancet 170 positioned beneath one of the number of spaced lancet cartridge openings 162 and a lancet lift rod 174 having a first lift rod end 180 connected to lancet 170 and a second lift rod end 182 slidably positioned through and past a cartridge bottom surface 184 a distance such that a force pushing upward on second lift rod end 182 causes a puncturing tip 196 of the lancet 170 to be raised through and past its respective spaced lancet cartridge opening 162.

Cartridge bottom surface 184 is positioned above the linear path of linear sliding, wedge shaped lift rod raising cam 114 a distance such that, when second lift rod end 182 is positioned above the second cam position, movement of wedge shaped lift rod raising cam 114 from the first cam position to the second cam position results in contact between wedge shaped lift rod raising cam 114 and second lift rod end 182 sufficient to cause puncturing tip 196 to be raised through and past its respective spaced lancet cartridge opening 162.

Electronic, micro-processor controlled control circuit 28 is in power receiving connection with the power connecting jack 14 and the battery holder 16, in controlling connection with the lancet lifting assembly solenoid 120, a turntable motor drive circuit 200 that interacts with indexing switch 20 to control dc motor 80, and counter display 52, and in input receiving connection from counter reset switch 56, on/off switch 54, and reed switch 22. Turntable motor drive circuit 200 is in controlling connection with the dc turntable drive motor 80 and in input receiving connection with turntable indexing switch 20.

Electronic, micro-processor controlled control circuit is programmed to a) move the indexable, motor driven turntable 18 until the puncturing tip 196 of a lancet 170 is in alignment with the lancet passage opening 72 when turned on with on/off switch 54; b) wait until a trigger signal is received from the reed switch 22, in this example the closing of reed contacts 108, 110; c) operate the lancet lifting assembly solenoid 120 to move the lift rod raising cam 114 from the first cam position to the second cam position and then back to the first cam position, in response to receiving the trigger signal frm the closing of reed switch 22; d) move the indexable, motor driven turntable 18 such that no puncturing tip 196 of a lancet 170 is in alignment with the lancet passage opening 72; and e) decrement the lancet counter display 52.

It can be seen from the preceding description that an automatic skin puncturing system has been provided.

It is noted that the embodiment of the automatic skin puncturing system described herein in detail for exemplary purposes is of course subject to many different variations in structure, design, application and methodology. Because many varying and different embodiments may be made within the scope of the inventive concept (s) herein taught, and because many modifications may be made in the embodiment herein detailed in accordance with the descriptive requirements of the law, it is to be understood that the details herein are to be interpreted as illustrative and not in a limiting sense.

What is claimed is:

1. An automatic skin puncturing system comprising:
   a housing assembly;
   a power connecting jack;
   a battery holder;
   an indexable, motor driven turntable;
   an index switch;
   a reed switch;
   a lancet lifting assembly;
   a disposable lancet carousel cartridge; and
   an electronic, micro-processor controlled circuit;
   the housing assembly including a bottom housing portion, a removable housing carousel cover portion and a securing knob;
   the bottom housing portion having a puncturing system cavity defined therein and accessible through a cartridge positioning opening formed through a top bottom housing portion surface, a triggering magnet opening formed through the top bottom housing portion surface at a location adjacent to the cartridge positioning opening, a power connecting jack opening, a battery compartment access cover, a counter display, an on/off switch, and a number of nonskid foot pads;
   the removable housing carousel cover portion being sized and securable to the bottom housing portion in a manner to cover the cartridge positioning opening with the securing knob, the removable housing carousel cover portion including a pivoting lancet lifting assembly trigger switch actuator having a top switch surface portion that is hingedly connected to and pivots with respect to a top cover surface of the removable housing carousel cover portion and a reed switch triggering magnet connected to a rod mechanically carried by the top switch surface portion that is positioned through the triggering magnet opening of the bottom housing portion when the top switch surface portion is oriented in parallel with the top cover surface of the removable housing carousel cover portion, the top switch surface portion including a finger positioning indentation having a lancet passage opening formed therethrough;
   the power connecting jack being positioned within the puncturing system cavity of the housing and adjacent the power connecting jack opening;
   the battery holder being positioned within the puncturing system cavity of the housing within a battery compartment and accessible by battery compartment access cover;
   the indexable, motor driven turntable being rotatable within the puncturing system cavity of the housing on a bearing pivot point extending upward from a bottom surface of the housing, the indexable, motor driven turntable being driven by a dc motor having a gear in connection with a perimeter rack gear formed around the underside of the turntable, a keyed carousel cartridge drive shaft extending upwardly from a center thereof, and a perimeter side edge having a number of index switch roller indentations formed thereon;
   the index switch being positioned within the puncturing system cavity of the housing and with respect to the indexable, motor driven turntable such that a roller of the index switch rolls along the perimeter side edge indexable, motor driven turntable;
   the index switch having open index switch contacts when the roller is positioned in one of the number of index switch roller indentations and closed open index switch contacts when the roller is not positioned in one of the number of index switch roller indentations;
   the reed switch being positioned within the housing at a location such that the reed switch triggering magnet is position in a location to close a pair of reed switch contacts when a user pushes down on the top switch surface portion;
   the lancet lifting assembly being positioned within the puncturing system cavity of the housing and including a main plate and a linear sliding, wedge shaped lift rod raising cam connected to the end of a lancet lifting assembly solenoid attached to the main plate;
   the lancet lifting assembly solenoid moving the wedge shaped lift rod raising cam along a linear path between a first cam position and a second cam position;
   the main plate having an adjustment wheel contact structure extending from a solenoid side end thereof;
   the main plate being supported by a main plate support fulcrum positioned under a cam side end of the main plate and contact between the adjustment wheel contact structure and an angled undersurface of a lancet depth adjustment wheel rotatably mounted to the bottom housing portion such that a portion of the lancet depth adjustment wheel extends out of the bottom housing portion, the height of the cam side end of the main plate being adjustable by positioning the lancet depth adjustment wheel;
   the disposable lancet carousel cartridge including a cartridge housing having a carousel hub formed through the center thereof having a key way adapted for receiving the upwardly projecting keyed carousel cartridge drive shaft of the indexable, motor driven turntable, an outer perimeter upper cartridge surface having a number of spaced lancet cartridge openings, and a number of lancet assemblies each with a lancet positioned beneath one of the number of spaced lancet cartridge openings and a lancet lift rod having a first end connected to the lancet and a second lift rod end slidably positioned through and past a cartridge bottom surface a distance such that a force pushing upward on the second lift rod end causes a puncturing tip of the lancet to be raised through and past its respective spaced lancet cartridge opening;
   the cartridge bottom surface being positioned above the linear path of the linear sliding, wedge shaped lift rod raising cam a distance such that, when a second lift rod end is positioned above the second cam position, movement of the wedge shaped lift rod raising cam from the first cam position to the second cam position results in contact between the wedge shaped lift rod raising cam and the second lift rod end sufficient to cause the puncturing tip of the lancet attached to the second lift rod end to be raised through and past its respective spaced lancet cartridge opening;
   the electronic, micro-processor controlled control circuit being in power receiving connection with the power connecting jack and the battery holder, in controlling connection with the lancet lifting assembly solenoid, the turntable motor drive circuit, and the counter display, and in input receiving connection from the counter reset switch, the on/off switch, and the reed switch;
   the turntable motor drive circuit being in controlling connection with the turntable drive motor and in input receiving connection with the turntable indexing switch;

the electronic, micro-processor controlled control circuit being programmed to a) move the indexable, motor driven turntable until the puncturing tip of a lancet in alignment with the lancet passage opening when turned on with the on/off switch; b) wait until a trigger signal is received from the reed switch; c) operate the lancet lifting assembly solenoid to move the lift rod raising cam from the first cam position to the second cam position and then back to the first cam position, in response to receiving the trigger signal; d) move the indexable, motor driven turntable such that no puncturing tip of a lancet is in alignment with the lancet passage opening; and e) decrement the lancet counter display.

* * * * *